United States Patent
Usui et al.

(10) Patent No.: US 11,618,724 B2
(45) Date of Patent: Apr. 4, 2023

(54) METHOD FOR PURIFYING 1,2-DIFLUOROETHYLENE (HFO-1132)

(71) Applicant: DAIKIN INDUSTRIES, LTD., Osaka (JP)

(72) Inventors: Takashi Usui, Osaka (JP); Kazuhiro Takahashi, Osaka (JP); Tomoyuki Iwamoto, Osaka (JP)

(73) Assignee: DAIKIN INDUSTRIES, LTD., Osaka (JP)

( * ) Notice: Subject to any disclaimer, the term of this patent is extended or adjusted under 35 U.S.C. 154(b) by 0 days.

(21) Appl. No.: 17/360,678

(22) Filed: Jun. 28, 2021

(65) Prior Publication Data

US 2021/0323899 A1 Oct. 21, 2021

Related U.S. Application Data

(63) Continuation of application No. PCT/JP2020/015656, filed on Apr. 7, 2020.

(30) Foreign Application Priority Data

Apr. 19, 2019 (JP) .............................. JP2019-079857

(51) Int. Cl.
  *C07C 17/389* (2006.01)
  *C07C 21/18* (2006.01)
(52) U.S. Cl.
  CPC ............ *C07C 17/389* (2013.01); *C07C 21/18* (2013.01)
(58) Field of Classification Search
  CPC .................................................. C07C 17/389
  See application file for complete search history.

(56) References Cited

U.S. PATENT DOCUMENTS

| 2016/0347693 A1 | 12/2016 | Fukushima et al. |
| 2017/0058171 A1 | 3/2017 | Fukushima et al. |
| 2017/0058172 A1* | 3/2017 | Fukushima .......... C10M 105/32 |

FOREIGN PATENT DOCUMENTS

| GB | 2 439 209 | 12/2007 | | |
| JP | 2013-241348 | 12/2013 | | |
| JP | 2013-241389 | 12/2013 | | |
| JP | 2016-011423 | 1/2016 | | |
| RU | 2 078 070 | 12/1994 | | |
| WO | 2015/125877 | 8/2015 | | |
| WO | 2015/186558 | 12/2015 | | |
| WO | WO-2019216175 A1 * | 11/2019 | ........... | C07C 17/354 |
| WO | WO-2019240233 A1 * | 12/2019 | ........... | B01J 27/132 |

OTHER PUBLICATIONS

WO2019216175A1, Machine translation, Nov. 2019, pp. 1-23 (Year: 2019).*
WO2019240233A1, Machine translation, Dec. 2019, pp. 1-23 (Year: 2019).*
Craig et al., "Thermodynamics of cis-trans Isomerizations. The 1,2-Difluoroethylenes", Journal of the American Chemical Society, Feb. 21, 1961, vol. 83, pp. 3047-3050.
International Search Report dated Jul. 14, 2020 in International (PCT) Application No. PCT/JP2020/015656.
Al-Dughaither, S. Abdullah et al., "HZSM-5 Zeolites with Different $SiO_2/AL_2O_3$ Ratios. Characterization and $NH_3$ Desorption Kinetics", Industrial & Engineering Chemistry Research, 2014, vol. 53, pp. 15303-15316.
Extended European Search Report dated Dec. 23, 2022 in European Patent Application No. 20791937.4.

* cited by examiner

*Primary Examiner* — Medhanit W Bahta
(74) *Attorney, Agent, or Firm* — Wenderoth, Lind & Ponack, L.L.P.

(57) ABSTRACT

The present disclosure provides a method for purifying HFO-1132 to a high purity while suppressing the isomerization and loss of HFO-1132. Specifically, the present disclosure provides a method for purifying 1,2-difluoroethylene, which is HFO-1132, the method comprising, in this order, step 1 of bringing a composition comprising trans-1,2-difluoroethylene, which is HFO-1132(E), and water into contact with a zeolite having an average pore size of 2 to 4 Å to reduce the water content from the composition; and step 2 of recovering a purified product containing HFO-1132(E) and a reduced content of water, and containing less than 0.1% by volume of HFO-1132(Z).

8 Claims, No Drawings

METHOD FOR PURIFYING 1,2-DIFLUOROETHYLENE (HFO-1132)

TECHNICAL FIELD

The present disclosure relates to a method for purifying 1,2-difluoroethylene (HFO-1132).

BACKGROUND ART 1,2-Difluoroethylene (HFO-1132) is referred to as a candidate of an alternative refrigerant component for mixed refrigerants of HFC, such as R410A (which is a mixed refrigerant of two components, i.e., HFC-32 and HFC-125) used as a refrigerant for air conditioners. HFO-1132 has two isomers, i.e., trans-1,2-difluoroethylene (HFO-1132(E)) and cis-1,2-difluoroethylene (HFO-1132(Z)).

A typically known purification method for reducing water and other impurities from a composition comprising HFO-1132 and water comprises bringing the composition into contact with a zeolite (molecular sieves), calcium chloride, silica gel, activated carbon, concentrated sulfuric acid, or the like to achieve dehydration. For example, Patent Literature (PTL) 1 discloses bringing a fluid comprising HFO-1132 into contact with a synthetic zeolite to achieve dehydration.

CITATION LIST

Patent Literature

PTL 1: WO2015/125877

SUMMARY

A method for purifying 1,2-difluoroethylene, which is HFO-1132, the method comprising, in this order,
step 1 of bringing a composition comprising trans-1,2-difluoroethylene, which is HFO-1132(E), and water into contact with a zeolite having an average pore size of 2 to 4 Å to reduce the water content from the composition; and
step 2 of recovering a purified product containing HFO-1132(E) and a reduced content of water, and containing less than 0.1% by volume of HFO-1132(Z).

Advantageous Effects

According to the present disclosure, HFO-1132 can be purified to a high purity while suppressing the isomerization and loss of HFO-1132.

DESCRIPTION OF EMBODIMENTS

The present disclosers conducted extensive research, and found that HFO-1132 can be purified to a high purity while suppressing the isomerization and loss of HFO-1132 by bringing a composition comprising HFO-1132 and water into contact with a specific zeolite when purifying HFO-1132 by reducing the water from the composition.

The present disclosure has been completed as a result of further research based on these findings.

The present disclosure encompasses the following embodiments.

In the present disclosure, unless otherwise specified, 1,2-difluoroethylene (HFO-1132) refers to trans-1,2-difluoroethylene (HFO-1132(E)) and/or cis-1,2-difluoroethylene (HFO-1132(Z)). More specifically, HFO-1132 refers to HFO-1132(E) alone, HFO-1132(Z) alone, or a mixture of HFO-1132(E) and HFO-1132(Z) (in any mixing ratio, unless otherwise specified). Further, a range indicated by "A to B" means A or more and B or less, unless otherwise specified.

The present disclosure is described below in detail by dividing the present disclosure into Embodiment 1, Embodiment 2, and Embodiment 3.

Method for Purifying HFO-1132 According to Embodiment 1

The disclosure of Embodiment 1 is based on the finding that HFO-1132 can be purified to a high purity while suppressing the isomerization and loss of HFO-1132 by bringing a composition comprising HFO-1132 and water into contact with a zeolite having an average pore size of 2 to 4 Å to reduce the water content from the composition. In particular, the degree of isomerization of HFO-1132 (isomerization percentage) in the purification process is less than 0.1% by volume (including the case where isomerization does not occur), and Embodiment 1 can be specified as follows when the disclosure according to Embodiment 1 is divided into a case in which the composition before purification is an HFO-1132(E)-rich composition (Embodiment 1-1), and a case in which the composition before purification is an HFO-1132(Z)-rich composition (Embodiment 1-2).

Embodiment 1-1: HFO-1132(E)-Rich Composition

A method for purifying 1,2-difluoroethylene, which is HFO-1132, the method comprising, in this order,
step 1 of bringing a composition comprising trans-1,2-difluoroethylene, which is HFO-1132(E), and water into contact with a zeolite having an average pore size of 2 to 4 Å to reduce the water content from the composition; and
step 2 of recovering a purified product containing HFO-1132(E) and a reduced content of water, and containing less than 0.1% by volume of HFO-1132(Z).

Embodiment 1-2: HFO-1132(Z)-Rich Composition

A method for purifying 1,2-difluoroethylene, which is HFO-1132, the method comprising, in this order,
step 1 of bringing a composition comprising cis-1,2-difluoroethylene, which is HFO-1132(Z), and water into contact with a zeolite having an average pore size of 2 to 4 Å to reduce the water content from the composition; and
step 2 of recovering a purified product containing HFO-1132(Z) and a reduced content of water, and containing less than 0.1% by volume of HFO-1132(E).

Examples of the composition comprising HFO-1132 and water include a composition comprising water that can be incorporated during the production of HFO-1132. Specific examples of the composition include a product of dehydrofluorination reaction of 1,1,2-trifluoroethane, and a product of isomerization reaction of HFO-1132(E) and/or HFO-1132(Z) in the presence of a metal catalyst.

The composition can also comprise impurities other than water. Examples of impurities include at least one member selected from intermediates, isomers, and by-products that can be incorporated during the production of HFO-1132 (e.g., hydrogen fluoride, fluoroethylene, difluoroethylene, trifluoroethylene, 1,1,1-trifluoroethane, propylene, acetylene, difluoromethane, trifluoromethane, and fluoromethane).

Embodiment 1-1 is, in particular, characterized in that a composition comprising HFO-1132(E) and water is used as the purification target, and a specific zeolite is used to achieve the degree of isomerization of HFO-1132(E) (isomerization percentage) during the purification process of less than 0.1% by volume (including the case where isomerization does not occur).

Thus, after the purification step (step 1), a purified product containing HFO-1132(E) and a reduced content of water, and containing less than 0.1% by volume of HFO-1132(Z) (including 0% by volume thereof, i.e., below the detection limit by gas chromatography) can be recovered in the recovery step (step 2).

Further, the use of a zeolite having an average pore size of 2 to 4 Å in the purification step (step 1) suppresses the adsorption of HFO-1132(E) to the zeolite; accordingly, the isomerization and loss of HFO-1132 can be suppressed, and HFO-1132 can be purified to a high purity. The composition before purification preferably does not substantially comprise HFO-1132(Z). For example, the composition before purification preferably comprises HFO-1132(Z) in an amount that cannot be detected by gas chromatography.

Embodiment 1-2 is, in particular, characterized in that a composition comprising HFO-1132(Z) and water is used as the purification target, and a specific zeolite is used to achieve the degree of isomerization of HFO-1132(Z) (isomerization percentage) during the purification process of less than 0.1% by volume (including the case where isomerization does not occur).

Thus, after the purification step (step 1), a purified product containing HFO-1132(Z) and a reduced content of water, and containing less than 0.1% by volume of HFO-1132(E) (including 0% by volume thereof, i.e., below the detection limit by gas chromatography) can be recovered in the recovery step (step 2).

Further, the use of a zeolite having an average pore size of 2 to 4 Å in the purification step (step 1) suppresses the adsorption of HFO-1132(Z) to the zeolite; accordingly, the isomerization and loss of HFO-1132 can be suppressed, and HFO-1132 can be purified to a high purity. The composition before purification preferably does not substantially comprise HFO-1132(E). For example, the composition before purification preferably comprises HFO-1132(E) in an amount that cannot be detected by gas chromatography.

Next, zeolites, which function as an adsorbent for adsorbing and removing water according to the present disclosure, are described. In the present disclosure, zeolites can adsorb and remove not only water, but also one or more impurities in addition to water; however, below, the adsorption and removal of water is particularly described.

Zeolites are a type of clay mineral, and are hydrous aluminosilicates containing alkali or alkaline earth metals with a rigid anionic framework with regular channels (tubular pores) and cavities.

Zeolites are typically represented by
$(M^{I}, M^{II}_{1/2})_m(Al_mSi_nO_{2(m+n)}) \cdot xH_2O$ (n≥m)
($M^{I}$: Li$^+$, Na$^+$, K$^+$, or the like, and $M^{II}$: Ca$^{2+}$, Mg$^{2+}$, Ba$^{2+}$, or the like), and
cations compensate the negative charge of the framework of the aluminosilicates.

The type of cations in zeolites is not limited, and the cations may be typically H$^+$, Li$^+$, Na$^+$, K$^+$, Ca$^{2+}$, Mg$^{2+}$, Ba$^{2+}$, and the like.

The basic structural unit of zeolites is a tetrahedral structure of SiO$_4$ or AlO$_4$ (together, TO$_4$ tetrahedron); these units infinitely continue in the three-dimensional direction to form crystals. Zeolite crystals are porous, and usually have a pore diameter of about 0.2 to 1.0 nm. Zeolites have molecular sieve properties, with which molecules that are larger than the pore size cannot enter into the pores. In addition to the molecular sieve effect of the pores based on their backbone structure, zeolites have properties such as solid acidity, ion exchange capacity, catalytic activity, and adsorption capacity.

In Embodiment 1, a composition comprising HFO-1132 and water is brought into contact with a zeolite having an average pore size of 2 to 4 Å to reduce the water content from the composition, whereby HFO-1132 can be purified to a high purity while suppressing the isomerization and loss of HFO-1132. In particular, the degree of isomerization of HFO-1132 (isomerization percentage) in the purification process is kept as low as less than 0.1% by volume (including the case where isomerization does not occur).

The use of a zeolite having an average pore size of 2 to 4 Å can improve the efficiency in terms of adsorption and removal of water while keeping the isomerization percentage of HFO-1132 and the possibility of HFO-1132 itself being adsorbed to the zeolite low; this enables HFO-1132 to be efficiently purified while keeping the loss in the purification step due to, for example, isomerization low.

Zeolites having an average pore size of 2 to 4 Å are commercially available. Examples include molecular sieves 3A (average pore size: 2 to 3 Å) and molecular sieves 4A (average pore size: 3 to 4 Å) (both produced by Union Showa K.K.). These zeolites may be used alone, or in a combination of two or more as long as they satisfy the requirement of the average pore size.

In the present disclosure, bringing a composition comprising HFO-1132 and water as a purification target into contact with a zeolite having an average pore size of 2 to 4 Å means allowing the composition to pass through a device (e.g., a column) filled with the zeolite, or introducing the composition into a container filled with the zeolite.

In the present disclosure, the zeolite is used as an adsorbent (a material for adsorbing and removing impurities). When the composition as the purification target is brought into contact with (allowed to pass through) the zeolite, water contained in the composition is adsorbed and removed by the zeolite.

In the present disclosure, to effectively adsorb and remove water, the composition as the purification target and the zeolite are preferably brought into contact in a mass ratio of about 100:1 to about 1:10, more preferably about 50:1 to about 1:5, and even more preferably about 10:1 to about 1:3. In the present disclosure, the amount of zeolite for use is, for example, such that 10 g of zeolite filling material (e.g., a stainless steel column) is used for about 10 to 100 g of the composition as the purification target.

In the present disclosure, the zeolite may be subjected to activation treatment before use. The conditions of the activation treatment are not limited. Examples include a drying treatment comprising, for example, heating in vacuum ($10^{-1}$ mmHg to $10^{-3}$ mmHg) overnight at a temperature of 200 to 350° C. In the present disclosure, however, zeolites that are not subjected to activation treatment can also be suitably used.

In the present disclosure, the mode of use of zeolites is not limited. The composition as the purification target may be allowed to pass through a device (e.g., a column) filled with the zeolite. Alternatively, the composition as the purification target may be introduced into a container filled with the zeolite, and a purified product may be recovered after a predetermined amount of time has elapsed.

In the present disclosure, the temperature at which the composition as the purification target is brought into contact with the zeolite is not limited; and is set in consideration of, for example, the boiling point of HFO-1132 contained in the composition as the purification target. Contacting at a lower temperature is usually preferred since side reactions (e.g., isomerization reactions) are suppressed at the time of contact. The temperature is preferably about 0 to 100° C. From this range, for example, a temperature of 0 to 50° C. or a temperature of 50 to 100° C. may be selected.

In the present disclosure, the time of bringing the composition as the purification target into contact with the zeolite is not limited, and may be freely set as long as the amount of impurities (including water) contained in the recovered product after purification can be reduced to a target degree or less. More specifically, the time may be set according to, for example, the passing-through speed, the filling time, and the temperature.

In the present disclosure, the zeolite for use may be in the form of powders, granules, or pellets. The zeolite may also be used as a molded body. Industrially, the zeolite is preferably used as a molded body. The shape of the molded body is not limited, and is preferably, for example, cylindrical with a diameter of about 0.5 to 5 mm and a length of about 1 to 15 mm, or spherical with a diameter of about 0.5 to 10 mm.

In the present disclosure, the method for producing a molded body of zeolite is not limited. For example, a conventionally known method that uses kaolin clay as a binder may be used.

In Embodiment 1-1, after the purification step (step 1), a purified product containing HFO-1132(E) and a reduced content of water, and containing less than 0.1% by volume of HFO-1132(Z) (including 0% by volume thereof, i.e., below the detection limit by gas chromatography) can be recovered in the recovery step (step 2). More specifically, since the isomerization percentage is kept as low as less than 0.1% by volume (preferably less than 0.01% by volume), the purity of HFO-1132(E) in the purified product can possibly be increased to preferably 99.9% by volume or higher. Further, the use of a specific zeolite suppresses the adsorption of HFO-1132(E), thus suppressing the loss of HFO-1132(E).

In Embodiment 1-2, after the purification step (step 1), a purified product containing HFO-1132(Z) and a reduced content of water, and containing less than 0.1% by volume of HFO-1132(E) (including 0% by volume thereof, i.e., below the detection limit by gas chromatography) can be recovered in the recovery step (step 2). More specifically, since the isomerization percentage is kept as low as less than 0.1% by volume (preferably less than 0.01% by volume), the purity of HFO-1132(Z) in the purified product can possibly be increased to preferably 99.9% by volume or higher. Further, the use of a specific zeolite suppresses the adsorption of HFO-1132(Z), thus suppressing the loss of HFO-1132(Z).

Method for Purifying HFO-1132 According to Embodiment 2

The disclosure of Embodiment 2 is based on the finding that HFO-1132 can be purified to a high purity while suppressing the isomerization and loss of HFO-1132 by bringing a composition comprising HFO-1132 and water into contact with a zeolite having an average pore size of 2 to 4 Å to reduce the water content from the composition. In particular, the degree of isomerization of HFO-1132 (isomerization percentage) in the purification process is kept low (including the case where isomerization does not occur), and Embodiment 2 can be specified as follows when the disclosure according to Embodiment 2 is divided into a case in which the composition before purification is an HFO-1132(E)-rich composition (Embodiment 2-1), a case in which the composition before purification is an HFO-1132(Z)-rich composition (Embodiment 2-2), and a case in which the composition before purification comprises HFO-1132(E) and HFO-1132(Z) in any mixing ratio (Embodiment 2-3).

Embodiment 2-1: HFO-1132(E)-Rich Composition

A method for purifying 1,2-difluoroethylene, which is HFO-1132, the method comprising
step 1 of allowing a composition comprising trans-1,2-difluoroethylene, which is HFO-1132(E), and water to pass through a column filled with a zeolite having an average pore size of 2 to 4 Å to reduce the water content from the composition,
wherein the isomerization percentage of the HFO-1132(E) and HFO-1132(Z) in passing through the column follows the following formulas:

$(1132(E)(\text{inlet \%})/(1132(E,Z)(\text{inlet \%}))-(1132(E)(\text{outlet \%})/(1132(E,Z)(\text{outlet \%}))<0.01$, and $(1132(Z)(\text{inlet \%})/(1132(E,Z)(\text{inlet \%}))-(1132(Z)(\text{outlet \%})/(1132(E,Z)(\text{outlet \%}))<|0.01|$.

Embodiment 2-2: HFO-1132(Z)-Rich Composition

A method for purifying 1,2-difluoroethylene, which is HFO-1132, the method comprising
step 1 of allowing a composition comprising cis-1,2-difluoroethylene, which is HFO-1132(Z), and water to pass through a column filled with a zeolite having an average pore size of 2 to 4 Å to reduce the water content from the composition,
wherein the isomerization percentage of the HFO-1132(E) and HFO-1132(Z) in passing through the column follows the following formulas:

$(1132(E)(\text{inlet \%})/(1132(E,Z)(\text{inlet \%}))-(1132(E)(\text{outlet \%})/(1132(E,Z)(\text{outlet \%}))<|0.01|$, and $(1132(Z)(\text{inlet \%})/(1132(E,Z)(\text{inlet \%}))-(1132(Z)(\text{outlet \%})/(1132(E,Z)(\text{outlet \%}))<0.01$.

Embodiment 2-3: Composition Comprising HFO-1132(E) and HFO-1132(Z) in Any Mixing Ratio A method for purifying 1,2-difluoroethylene, which is HFO-1132, the method comprising
allowing a composition comprising trans-1,2-difluoroethylene, which is HFO-1132(E), cis-1,2-difluoroethylene, which is HFO-1132(Z), and water to pass through a column filled with a zeolite having an average pore size of 2 to 4 Å to reduce the water content from the composition,
wherein the isomerization percentage of the HFO-1132(E) and HFO-1132(Z) in passing through the column follows the following formulas:

$(1132(E)(\text{inlet \%})/(1132(E,Z)(\text{inlet \%}))-(1132(E)(\text{outlet \%})/(1132(E,Z)(\text{outlet \%}))<|0.01|$, and $(1132(Z)(\text{inlet \%})/(1132(E,Z)(\text{inlet \%}))-(1132(Z)(\text{outlet \%})/(1132(E,Z)(\text{outlet \%}))<|0.01|$.

The general description for the above composition comprising HFO-1132 and water (purification target) is the same as that described for Embodiment 1.

Embodiment 2-1 is, in particular, characterized in that a composition comprising HFO-1132(E) and water is used as the purification target, and a zeolite having an average pore size of 2 to 4 Å is used as an adsorbent to keep the degree of isomerization of HFO-1132(E) (isomerization percentage) during the purification process (dehydration process) low (including the case where isomerization does not occur).

Thus, before (at the column inlet) and after (at the column outlet) the purification step, the isomerization percentage of the HFO-1132(E) and the HFO-1132(Z) in passing through the column follows the following formulas:

(1132(E)(inlet %)/(1132(E,Z)(inlet %))−(1132(E)(outlet %)/(1132(E,Z)(outlet %))<0.01, and (1132(Z)(inlet %)/(1132(E,Z)(inlet %))−(1132(Z)(outlet %)/(1132(E,Z)(outlet %))<|0.01|.

Further, the use of a zeolite having an average pore size of 2 to 4 Å in the purification step suppresses the adsorption of HFO-1132(E) to the zeolite; accordingly, the isomerization and loss of HFO-1132 can be suppressed, and HFO-1132 can be purified to a high purity. The composition before purification preferably does not substantially comprise HFO-1132(Z). For example, the composition before purification preferably comprises HFO-1132(Z) in an amount that cannot be detected by gas chromatography.

Embodiment 2-2 is, in particular, characterized in that a composition comprising HFO-1132(Z) and water is used as the purification target, and a zeolite having an average pore size of 2 to 4 Å is used as an adsorbent to keep the degree of isomerization of HFO-1132(Z) (isomerization percentage) during the purification process (dehydration process) low (including the case where isomerization does not occur).

Thus, before (at the column inlet) and after (at the column outlet) the purification step, the isomerization percentage of the HFO-1132(E) and HFO-1132(Z) in passing through the column follows the following formulas:

(1132(E)(inlet %)/(1132(E,Z)(inlet %))−(1132(E)(outlet %)/(1132(E,Z)(outlet %))<|0.01|, and (1132(Z)(inlet %)/(1132(E,Z)(inlet %))−(1132(Z)(outlet %)/(1132(E,Z)(outlet %))<0.01.

Further, the use of a zeolite having an average pore size of 2 to 4 Å in the purification step suppresses the adsorption of HFO-1132(Z) to the zeolite; accordingly, the isomerization and loss of HFO-1132 can be suppressed, and HFO-1132 can be purified to a high purity. The composition before purification preferably does not substantially comprise HFO-1132(E). For example, the composition before purification preferably comprises HFO-1132(E) in an amount that cannot be detected by gas chromatography.

Embodiment 2-3 is, in particular, characterized in that a composition comprising HFO-1132(E), HFO-1132(Z), and water is used as the purification target, and a zeolite having an average pore size of 2 to 4 Å is used as an adsorbent to keep the degree of isomerization of HFO-1132 (isomerization percentage) during the purification process low (including the case where isomerization does not occur).

Thus, before (at the column inlet) and after (at the column outlet) the purification step, the isomerization percentage of the HFO-1132(E) and HFO-1132(Z) in passing through the column follows the following formulas:

(1132(E)(inlet %)/(1132(E,Z)(inlet %))−(1132(E)(outlet %)/(1132(E,Z)(outlet %))<|0.01|, and (1132(Z)(inlet %)/(1132(E,Z)(inlet %))−(1132(Z)(outlet %)/(1132(E,Z)(outlet %))<|0.01|.

Further, the use of a zeolite having an average pore size of 2 to 4 Å in the purification step suppresses the adsorption of HFO-1132 to the zeolite; accordingly, the isomerization and loss of HFO-1132 can be suppressed, and HFO-1132 can be purified to a high purity.

The description for the zeolite according to the present disclosure is the same as the description for Embodiment 1.

In the present disclosure, the composition as the purification target is allowed to pass through (contact with) a column filled with the zeolite as an adsorbent (a material for adsorbing and removing impurities), so that water contained in the composition is adsorbed and removed by the zeolite.

In the present disclosure, to effectively adsorb and remove water, the composition as the purification target and the zeolite are preferably brought into contact in a mass ratio of about 100:1 to about 1:10, more preferably about 50:1 to about 1:5, and even more preferably about 10:1 to about 1:3. In the present disclosure, the amount of zeolite for use is, for example, such that 10 g of zeolite filling material (e.g., a stainless steel column) is used for about 10 to 100 g of the composition as the purification target.

Also, to effectively adsorb and remove water, the contact time between the composition as the purification target and the zeolite by passing through is preferably about 0.01 to 60 minutes, more preferably about 0.1 to 30 minutes, and even more preferably about 0.3 to 10 minutes.

In the present disclosure, the temperature at which the composition as the purification target is brought into contact with the zeolite is not limited, and is set in consideration of, for example, the boiling point of HFO-1132 contained in the composition as the purification target. Contacting at a lower temperature is usually preferred since side reactions (e.g., isomerization reactions) are suppressed at the time of contact. The temperature is preferably about 0 to 100° C. From this range, for example, a temperature of 0 to 50° C. or a temperature of 50 to 100° C. may be selected.

In the present disclosure, the time of bringing the composition as the purification target into contact with the zeolite is not limited, and may be freely set as long as the water content in the recovered product after purification can be reduced to a target degree or less. More specifically, the time may be set according to, for example, the amount of the zeolite used, the contact time, and the temperature. In Embodiments 2-1 to 2-3, the isomerization percentage, in absolute value, is less than 0.01, and preferably less than 0.001.

In the present disclosure, the zeolite for use may be in the form of powders, granules, or pellets. The zeolite may also be used as a molded body. Industrially, the zeolite is preferably used as a molded body. The shape of the molded body is not limited, and is preferably, for example, cylindrical with a diameter of about 0.5 to 5 mm and a length of about 1 to 15 mm, or spherical with a diameter of about 0.5 to 10 mm.

In the present disclosure, the method for producing a molded body of zeolites is not limited. For example, a conventionally known method that uses kaolin clay as a binder may be used.

Method for Purifying HFO-1132 According to Embodiment 3

The disclosure of Embodiment 3 is based on the finding that HFO-1132 can be purified to a high purity while suppressing the isomerization and loss of HFO-1132 by bringing a composition comprising HFO-1132 and water into contact with a zeolite with an $SiO_2/Al_2O_3$ ratio of 5.0 or more to reduce the water content from the composition. In particular, the degree of isomerization of HFO-1132 (isomerization percentage) in the purification process is kept low (including the case where isomerization does not occur). The isomerization percentage is preferably less than 0.1% by volume.

The method for purifying HFO-1132 according to Embodiment 3 can be specified as follows.

A method for purifying 1,2-difluoroethylene, which is HFO-1132, the method comprising bringing a composition comprising trans-1,2-difluoroethylene, which is HFO-1132(E), and/or cis-1,2-difluoroethylene, which is HFO-1132(Z), and water into contact with a zeolite with an $SiO_2/Al_2O_3$ ratio of 5.0 or more to reduce the water content from the composition.

The general description for the above composition comprising HFO-1132 and water (purification target) is the same as that described for Embodiment 1. The total content of HFO-1132(E) and HFO-1132(Z) in the composition may be set widely from a range of, for example, 10 to 99.99% by volume.

Embodiment 3 is, in particular, characterized in that a composition comprising HFO-1132(E) and/or HFO-1132 (Z), and water is used as the purification target, and a specific zeolite is used to keep the degree of isomerization of HFO-1132 (isomerization percentage) during the purification process low, preferably as low as less than 0.1% by volume (including the case where isomerization does not occur).

Thus, after the purification step, a purified product that contains a reduced content of water and in which the isomerization of HFO-1132 is suppressed (variation in the ratio of E/Z % by volume is suppressed) can be recovered in the recovery step. Further, the use of a zeolite with an $SiO_2/Al_2O_3$ ratio of 5.0 or more in the purification step suppresses the adsorption of HFO-1132 to the zeolite; accordingly, the isomerization and loss of HFO-1132 can be suppressed, and HFO-1132 can be purified to a high purity.

The description for the zeolite according to Embodiment 3 is the same as the description for Embodiment 1, except that a zeolite with an $SiO_2/Al_2O_3$ ratio of 5.0 or more is used. In Embodiment 3, the upper limit of the $SiO_2/Al_2O_3$ ratio in the zeolite is not limited, and may be about 2000. That is, the $SiO_2/Al_2O_3$ ratio is preferably 5.0 or more and 2,000 or less, and more preferably 5 or more and 100 or less.

In Embodiment 3, a composition comprising HFO-1132 and water is brought into contact with a zeolite with an $SiO_2/Al_2O_3$ ratio of 5.0 or more to reduce the water content from the composition, whereby HFO-1132 can be purified to a high purity while suppressing the isomerization and loss of HFO-1132. In particular, the degree of isomerization of HFO-1132 (isomerization percentage) in the purification process is kept low, preferably as low as less than 0.1% by volume (more preferably less than 0.01% by volume) (including 0% by volume thereof, i.e., below the detection limit by gas chromatography).

Since the $SiO_2/Al_2O_3$ ratio is 5.0 or more, the efficiency in terms of adsorption and removal of water can be improved while keeping the isomerization percentage of HFO-1132 and the possibility of HFO-1132 itself being adsorbed to the zeolite low, which enables HFO-1132 to be efficiently purified while keeping the loss in the purification step due to, for example, isomerization low.

Zeolites with an $SiO_2/Al_2O_3$ ratio of 5.0 or more are commercially available. Examples include ZSM-5 (produced by Tosoh Corporation) and ferrierite (produced by Tosoh Corporation). These zeolites may be used alone, or in a combination of two or more as long as they satisfy the requirement of the $SiO_2/Al_2O_3$ ratio.

In Embodiment 3, the method, conditions, etc., for bringing the composition as the purification target comprising HFO-1132 and water into contact with a zeolite with an $SiO_2/Al_2O_3$ ratio of 5.0 or more are the same as those for Embodiment 1.

Purified Product with Reduced Water Content

As described above, the methods for purifying HFO-1132 according to the present disclosure are capable of purifying HFO-1132 to a high purity while suppressing the isomerization and loss of HFO-1132 by bringing a composition comprising HFO-1132 and water into contact with a specific zeolite to reduce the water content from the composition. The purified product containing a reduced content of water obtained through the purification methods above can be specified as follows.

A purified product containing trans-1,2-difluoroethylene (HFO-1132(E)) and/or cis-1,2-difluoroethylene (HFO-1132 (Z)), and water, wherein the water content is 100 ppm (w/w) or less.

The embodiments according to the present disclosure are described above; however, various changes in forms and details can be made without departing from the spirit and scope of the claims.

Accordingly, the present disclosure includes the following subject matter.

Item 1. A method for purifying 1,2-difluoroethylene, which is HFO-1132, the method comprising, in this order,
step 1 of bringing a composition comprising trans-1,2-difluoroethylene, which is HFO-1132(E), and water into contact with a zeolite having an average pore size of 2 to 4 Å to reduce the water content from the composition; and
step 2 of recovering a purified product containing HFO-1132(E) and a reduced content of water, and containing less than 0.1% by volume of HFO-1132(Z).

Item 2. A method for purifying 1,2-difluoroethylene, which is HFO-1132, the method comprising, in this order,
step 1 of bringing a composition comprising cis-1,2-difluoroethylene, which is HFO-1132(Z), and water into contact with a zeolite having an average pore size of 2 to 4 Å to reduce the water content from the composition; and
step 2 of recovering a purified product containing HFO-1132(Z) and a reduced content of water, and containing less than 0.1% by volume of HFO-1132(E).

Item 3. A method for purifying 1,2-difluoroethylene, which is HFO-1132, the method comprising
step 1 of allowing a composition comprising trans-1,2-difluoroethylene, which is HFO-1132(E), and water to pass through a column filled with a zeolite having an average pore size of 2 to 4 Å to reduce the water content from the composition,
wherein the isomerization percentage of the HFO-1132(E) and HFO-1132(Z) in passing through the column follows the following formulas:

$$(1132(E)(\text{inlet }\%)/(1132(E,Z)(\text{inlet }\%))-(1132(E)(\text{outlet }\%)/(1132(E,Z)(\text{outlet }\%))<0.01, \text{ and}$$

$$(1132(Z)(\text{inlet }\%)/(1132(E,Z)(\text{inlet }\%))-(1132(Z)(\text{outlet }\%)/(1132(E,Z)(\text{outlet }\%))<|0.01|.$$

Item 4. A method for purifying 1,2-difluoroethylene, which is HFO-1132, the method comprising
step 1 of allowing a composition comprising cis-1,2-difluoroethylene, which is HFO-1132(Z), and water to pass through a column filled with a zeolite having an average pore size of 2 to 4 Å to reduce the water content from the composition, wherein the isomerization percentage of the HFO-1132(E) and HFO-1132(Z) in passing through the column follows the following formulas:

$$(1132(E)(\text{inlet }\%)/(1132(E,Z)(\text{inlet }\%))-(1132(E)(\text{outlet }\%)/(1132(E,Z)(\text{outlet }\%))<|0.01|, \text{ and}$$

$$(1132(Z)(\text{inlet }\%)/(1132(E,Z)(\text{inlet }\%))-(1132(Z)(\text{outlet }\%)/(1132(E,Z)(\text{outlet }\%))<0.01.$$

Item 5. A method for purifying 1,2-difluoroethylene, which is HFO-1132, the method comprising step 1 of allowing a composition comprising trans-1,2-difluoroethylene, which is HFO-1132(E), cis-1,2-difluoroethylene, which is HFO-1132(Z), and water to pass through a column filled with a zeolite having an average pore size of 2 to 4 Å to reduce the water content from the composition, wherein the isomerization percentage of the HFO-1132(E) and HFO-1132(Z) in passing through the column follows the following formulas:

$$(1132(E)(\text{inlet }\%)/(1132(E,Z)(\text{inlet }\%))-(1132(E)(\text{outlet }\%)/(1132(E,Z)(\text{outlet }\%))<|0.01|, \text{ and}$$

$$(1132(Z)(\text{inlet }\%)/(1132(E,Z)(\text{inlet }\%))-(1132(Z)(\text{outlet }\%)/(1132(E,Z)(\text{outlet }\%))<|0.01|.$$

Item 6. The method for purifying HFO-1132 according to any one of Items 1 to 5, wherein step 1 is performed at a temperature of 0 to 100° C.

Item 7. The purification method according to any one of Items 1 to 6, wherein the zeolite is molecular sieves 3A and/or molecular sieves 4A.

Item 8. A method for purifying 1,2-difluoroethylene, which is HFO-1132, the method comprising bringing a composition comprising trans-1,2-difluoroethylene, which is HFO-1132(E), and/or cis-1,2-difluoroethylene, which is HFO-1132(Z), and water into contact with a zeolite with an $SiO_2/Al_2O_3$ ratio of 5.0 or more to reduce the water content from the composition.

Item 9. The method for purifying HFO-1132 according to Item 8, wherein the isomerization percentage of the HFO-1132 in the step is less than 0.1% by volume.

Item 10. The method for purifying HFO-1132 according to Item 8 or 9, wherein the step is performed at a temperature of 0 to 100° C.

Item 11. The method for purifying HFO-1132 according to any one of Items 8 to 10, wherein the zeolite is ZSM-5.

Item 12. The method for purifying HFO-1132 according to any one of Items 1 to 11, wherein the composition further comprises at least one member selected from the group consisting of fluoroethylene, difluoroethylene, trifluoroethylene, 1,1,1-trifluoroethane, and propylene.

Item 13. The method for purifying HFO-1132 according to any one of Items 1 to 12, wherein the composition is a product of dehydrofluorination reaction of 1,1,2-trifluoroethane.

Item 14. The method for purifying HFO-1132 according to any one of Items 1 to 12, wherein the composition is a product of isomerization reaction of HFO-1132(E) and/or HFO-1132(Z) in the presence of a metal catalyst.

Item 15. A purified product containing trans-1,2-difluoroethylene, which is HFO-1132(E), and water, wherein the HFO-1132(E) content is 99.9% by volume or more, and the water content is 100 ppm (w/w) or less.

Item 16. A purified product containing cis-1,2-difluoroethylene, which is HFO-1132(Z), and water, wherein the HFO-1132(Z) content is 99.9% by volume or more, and the water content is 100 ppm (w/w) or less.

EXAMPLES

The present disclosure is described in detail below with reference to Examples and Comparative Examples. However, the present disclosure is not limited to the Examples.

In the Examples and Comparative Examples, the purity of HFO-1132 and the impurity concentration were measured with the following measuring device under the following measuring conditions. The water content was measured with the following moisture meter.

Measuring device: gas chromatography (with an FID detector)

Measurement conditions: GS-GasPro column

Calculation of purity: calculated using the GC peak area ratio

Measurement of water content: measured with a Karl Fischer moisture meter.

Example 1

Five grams of molecular sieves 3A (average pore size: 2 to 3 Å, $SiO_2/Al_2O_3$ ratio: 2.0) were weighed and added to a cylinder, followed by vacuum-drying at 250° C. for 2 hours.

After drying, the resulting product was allowed to cool to room temperature, and 10 g of gas containing trans-1,2-difluoroethylene (HFO-1132(E)) (water content: 200 ppm) was added to the cylinder, followed by heating at 50° C. for 3 hours.

After heating, the resulting product was allowed to cool, and the gas in the cylinder was recovered by vacuum-degassing and subjected to composition analysis by gas chromatography.

Example 2

The same procedure was performed as in Example 1, except that the heating temperature (50° C.) was changed to 100° C.

Example 3

The same procedure was performed as in Example 1, except that molecular sieves 4A (average pore size: 3 to 4 Å, $SiO_2/Al_2O_3$ ratio: 2.0) were used.

Example 4

The same procedure was performed as in Example 1, except that molecular sieves 4A were used, and the heating temperature (50° C.) was changed to 100° C.

Example 5

The same procedure was performed as in Example 1, except that ZSM-5 ($SiO_2/Al_2O_3$ ratio: 40.0) was used.

Example 6

The same procedure was performed as in Example 1, except that ZSM-5 was used, and the heating temperature (50° C.) was changed to 100° C.

Comparative Example 1

The same procedure was performed as in Example 1, except that molecular sieves 5A (average pore size: more than 4 Å, $SiO_2/Al_2O_3$ ratio: 2.0) were used.

Comparative Example 2

The same procedure was performed as in Example 1, except that molecular sieves 5A were used, and the heating temperature (50° C.) was changed to 100° C.

TABLE 1

| | Starting material | Ex. 1 Molecular sieves 3A | Ex. 2 Molecular sieves 3A | Ex. 3 Molecular sieves 4A | Ex. 4 Molecular sieves 4A | Comp. Ex. 1 Molecular sieves 5A | Comp. Ex. 2 Molecular sieves 5A | Ex. 5 ZSM-5 | Ex. 6 ZSM-5 |
|---|---|---|---|---|---|---|---|---|---|
| Heating temperature (° C.) | — | 50 | 100 | 50 | 100 | 50 | 100 | 50 | 100 |
| Water content (ppm) | 202 | 11 | 10 | 7 | 9 | 13 | 15 | 19 | 21 |
| HFO-1132(E) (%) | 95.14 | 95.08 | 95.09 | 94.89 | 94.79 | 92.84 | 91.64 | 95.16 | 95.08 |
| HFO-1132(Z) (%) | trace | trace | trace | 0.02 | 0.03 | 0.35 | 1.49 | trace | trace |
| HFO-1123 (%) | 0.03 | 0.03 | 0.03 | 0.03 | 0.02 | 0.03 | 0.03 | 0.02 | 0.02 |
| HFC-32 (%) | 0.01 | 0.01 | 0.01 | trace | trace | trace | trace | trace | trace |
| HFO-1141 (%) | 0.07 | 0.06 | 0.06 | 0.06 | 0.05 | 0.06 | 0.06 | 0.06 | 0.06 |
| HFC-143a (%) | 4.69 | 4.76 | 4.75 | 4.96 | 5.06 | 6.72 | 6.78 | 4.71 | 4.80 |
| Propylene (%) | 0.06 | 0.06 | 0.06 | 0.04 | 0.05 | trace | trace | 0.05 | 0.04 |

The results shown in Table 1 clearly indicate that the methods for purifying HFO-1132 of Examples 1 to 6, which use a zeolite having an average pore size of 2 to 4 Å or a zeolite with an $SiO_2/Al_2O_3$ ratio of 5.0 or more, are capable of purifying HFO-1132 to a high purity while suppressing the isomerization and loss of HFO-1132.

The invention claimed is:

1. A method for purifying 1,2-difluoroethylene, which is HFO-1132, during the production of HFO-1132(E), the method comprising, in this order,
    step 1 of bringing a composition consisting essentially of trans-1,2-difluoroethylene, which is HFO-1132(E), intermediates and/or by-products incorporated during the production of HFO-1132(E), and water into contact with a zeolite having an average pore size of 2 to 4 Å at a temperature of 50 to 100° C. to reduce the water content from the composition; and
    step 2 of recovering a purified product containing HFO-1132(E) and a reduced content of water, and containing less than 0.1% by volume of HFO-1132(Z).

2. A method for purifying 1,2-difluoroethylene, which is HFO-1132, during the production of HFO-1132(Z), the method comprising, in this order,
    step 1 of bringing a composition consisting essentially of cis-1,2-difluoroethylene, which is HFO-1132(Z), intermediates and/or by-products incorporated during the production of HFO-1132(Z), and water into contact with a zeolite having an average pore size of 2 to 4 Å at a temperature of 50 to 100° C. to reduce the water content from the composition; and
    step 2 of recovering a purified product containing HFO-1132(Z) and a reduced content of water, and containing less than 0.1% by volume of HFO-1132(E).

3. A method for purifying 1,2-difluoroethylene, which is HFO-1132, during the production of HFO-1132(E), the method comprising
    step 1 of allowing a composition consisting essentially of trans-1,2-difluoroethylene, which is HFO-1132(E), intermediates and/or by-products incorporated during the production of HFO-1132(E), and water to pass through a column filled with a zeolite having an average pore size of 2 to 4 Å at a temperature of 50 to 100° C. to reduce the water content from the composition,
    wherein an isomerization percentage of the HFO-1132(E) and HFO-1132(Z) in passing through the column follows the following formulas:
    (1132(E) (inlet %)/(1132(E,Z) (inlet %))−(1132(E) (outlet %)/(1132(E,Z) (outlet %))<0.01, and
    (1132(Z) (inlet %)/(1132(E,Z) (inlet %))−(1132(Z) (outlet %)/(1132(E,Z) (outlet %))<|0.01|.

4. A method for purifying 1,2-difluoroethylene, which is HFO-1132, during the production of HFO-1132(Z), the method comprising
    step 1 of allowing a composition consisting essentially of cis-1,2-difluoroethylene, which is HFO-1132(Z), intermediates and/or by-products incorporated during the production of HFO-1132(Z), and water to pass through a column filled with a zeolite having an average pore size of 2 to 4 Å at a temperature of 50 to 100° C. to reduce the water content from the composition,
    wherein an isomerization percentage of the HFO-1132(E) and HFO-1132(Z) in passing through the column follows the following formulas:
    (1132(E) (inlet %)/(1132(E,Z) (inlet %))−(1132(E) (outlet %)/(1132(E,Z) (outlet %))<|0.01|, and
    (1132(Z) (inlet %)/(1132(E,Z) (inlet %))−(1132(Z) (outlet %)/(1132(E,Z) (outlet %))<0.01.

5. The purification method according to claim 1, wherein the zeolite is molecular sieves 3A and/or molecular sieves 4A.

6. The method for purifying HFO-1132 according to claim 1, wherein the composition comprises at least one member selected from the group consisting of fluoroethylene, trifluoroethylene, 1,1,1-trifluoroethane, and propylene.

7. The method for purifying HFO-1132 according to claim 1, wherein, before step 1, the composition comprising trans-1,2-difluoroethylene is prepared by a dehydrofluorination reaction of 1,1,2-trifluoroethane.

8. The method for purifying HFO-1132 according to claim 1, wherein, before step 1, the composition comprising trans-1,2-difluoroethylene is prepared by a isomerization reaction of HFO-1132(E) and/or HFO-1132(Z) in the presence of a metal catalyst.

* * * * *